United States Patent
Moskal

(10) Patent No.: US 10,757,219 B2
(45) Date of Patent: *Aug. 25, 2020

(54) SECURE NETWORK ACCESS TO MEDICAL DEVICE

(71) Applicant: Fenwal, Inc., Lake Zurich, IL (US)

(72) Inventor: Witold Moskal, Park Ridge, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/382,998

(22) Filed: Apr. 12, 2019

(65) Prior Publication Data

US 2019/0245942 A1 Aug. 8, 2019

Related U.S. Application Data

(63) Continuation of application No. 15/331,441, filed on Oct. 21, 2016, now Pat. No. 10,306,012.

(Continued)

(51) Int. Cl.
*H04L 29/08* (2006.01)
*G16H 40/67* (2018.01)
(Continued)

(52) U.S. Cl.
CPC ............ *H04L 67/32* (2013.01); *A61M 5/142* (2013.01); *A61M 5/172* (2013.01);
(Continued)

(58) Field of Classification Search
CPC ..... H04W 12/06; H04W 12/08; H04W 12/00; H04L 63/20; H04L 63/10; H04L 67/42;
(Continued)

(56) References Cited

U.S. PATENT DOCUMENTS 6,519,569 B1 * 2/2003 White .................... G16H 20/17
705/3
7,647,237 B2 * 1/2010 Malave ................. A61M 5/172
705/3

(Continued)

FOREIGN PATENT DOCUMENTS

EP 3173959 A1 5/2017

OTHER PUBLICATIONS

Ankarali et al. "A comparative review on the wireless implantable medical devices privacy and security" IEEE 2014 (Year: 2014).*

(Continued)

*Primary Examiner* — David R Lazaro

(74) *Attorney, Agent, or Firm* — Becker Patent Law, LLC

(57) ABSTRACT

A method of improving network access security on a medical device includes opening a communication port on the medical device to establish a communication session on a network and transmitting medical device data to a computer over the network during the communication session. After the medical device data is transmitted to the computer, the method includes transmitting to the computer a request for a command from the computer during the communication session. The method also includes receiving a command from the computer, processing the command, and closing the communication port on the medical device.

20 Claims, 10 Drawing Sheets

Related U.S. Application Data

(60) Provisional application No. 62/260,083, filed on Nov. 25, 2015.

(51) Int. Cl.
    *G06F 19/00*     (2018.01)
    *A61M 5/142*     (2006.01)
    *A61M 5/172*     (2006.01)
    *H04L 29/06*     (2006.01)
    *G16H 20/17*     (2018.01)

(52) U.S. Cl.
    CPC ...... *G06F 19/3418* (2013.01); *G06F 19/3468* (2013.01); *G16H 20/17* (2018.01); *G16H 40/67* (2018.01); *H04L 67/42* (2013.01); *A61M 2205/3569* (2013.01); *A61M 2205/3584* (2013.01); *A61M 2205/50* (2013.01); *A61M 2205/52* (2013.01)

(58) Field of Classification Search
    CPC ....... H04L 63/08; H04L 67/141; H04L 63/02; H04L 63/0876; G06F 21/6218; G06F 21/62; A61B 5/0022
    See application file for complete search history.

(56) References Cited

U.S. PATENT DOCUMENTS

| | | | |
|---|---|---|---|
| 7,933,780 B2* | 4/2011 | De La Huerga | A61M 5/14212 705/2 |
| 8,694,600 B2* | 4/2014 | Gaines | G06F 19/3418 709/217 |
| 8,905,959 B2 | 12/2014 | Basaglia | |
| 9,479,526 B1* | 10/2016 | Yang | G06F 21/577 |
| 10,306,012 B2* | 5/2019 | Moskal | G16H 20/17 |
| 2002/0082728 A1 | 6/2002 | Mueller et al. | |
| 2004/0138835 A1 | 7/2004 | Ransom et al. | |
| 2007/0155208 A1* | 7/2007 | Pirzada | A61M 16/0069 439/144 |
| 2009/0156991 A1 | 6/2009 | Roberts et al. | |
| 2013/0031201 A1 | 1/2013 | Kagan et al. | |
| 2013/0163584 A1* | 6/2013 | Jayaraman | H04L 65/1036 370/352 |
| 2014/0173082 A1* | 6/2014 | Shin | G16H 40/67 709/223 |
| 2014/0237561 A1* | 8/2014 | Mraz | H04L 63/10 726/5 |
| 2015/0141955 A1* | 5/2015 | Ruchti | G16H 20/17 604/506 |
| 2016/0095976 A1* | 4/2016 | Simpson | G16H 20/17 604/66 |
| 2016/0294951 A1* | 10/2016 | Durrant | H02J 7/0047 |
| 2017/0149567 A1* | 5/2017 | Moskal | H04W 12/10 |
| 2017/0149929 A1* | 5/2017 | Moskal | G16H 20/17 |
| 2017/0372600 A1* | 12/2017 | Palin | H04L 67/2804 |
| 2018/0126067 A1* | 5/2018 | Ledford | A61M 5/172 |
| 2019/0245942 A1* | 8/2019 | Moskal | A61M 5/142 |

OTHER PUBLICATIONS

Hei et al. "PIPAC: Patient Infusion Pattern based Access Control Scheme for Wireless Insulin Pump System" 2013 Proceedings IEEE Infocom (Year: 2013).*

Li et al. "Hijacking an Insulin Pump: Security Attacks and Defenses for a Diabetes Therapy System" 2011 IEEE 13th International Conference on e-Health Networking, Applications and Services (Year: 2011).*

Paul et al. "A Review of the Security of Insulin Pump Infusion Systems" Journal of Diabetes Science and Technology vol. 5, Issue 6, Nov. 2011 (Year: 2011).*

Creutzburg et al. "Security risk of medical devices in IT networks—the case of an infusion pump unit" Proceedings of SPIE—The International Society for Optical Engineering Mar. 2015 (Year: 2015).

European Search Report and Annex, European Patent Application No. 16197653, dated Apr. 19, 2017; 11 pages.

Jay Ribak; "Active FTP vs. Passive FTP, a Definitive Explanation," Sep. 30, 2005, Retrieved from the Internet on Mar. 30, 2017; URL:https://web-beta.archive.org/web/20050930214951/http://slacksite.com/other/ftp.html.

Amendments received before examination in European Pat. App. 16197653.5, dated Nov. 7, 2017, 14 pages.

Communication from the Examining Division in European Pat. App. 16197653.5, dated May 7, 2019, 7 pages.

Reply to Communication in EP 16197653.3, dated Sep. 2, 2019, 51 pages.

* cited by examiner

US 10,757,219 B2

SECURE NETWORK ACCESS TO MEDICAL DEVICE

CROSS-REFERENCE TO RELATED APPLICATIONS

This application is a continuation of U.S. application Ser. No. 15/331,441, filed Oct. 21, 2016, which claims the benefit of U.S. Provisional Application No. 62/260,083, filed Nov. 25, 2015, both of which are herein incorporated by reference in their entireties.

BACKGROUND

Infusion pumps are used to administer drugs and other medicaments to patients, typically in a clinical setting. An infusion pump provides a controlled amount of the medicament over time to the patient. The amount is administered pursuant to parameters entered by a clinician into the pump using a pump user interface.

Some infusion pumps can be monitored or controlled remotely over a network. This introduces the potential of a security threat, since a cyber attacker could take remote control of the system and change the amount of medicament administered to a patient.

DETAILED DESCRIPTION OF ILLUSTRATIVE EMBODIMENTS

One or more embodiments described herein may allow a server to require an infusion pump to perform a command.

One or more embodiments described herein may allow a server computer to receive infusion data from a pump in a secure manner.

One or more embodiments described herein may enable a server computer to recover missing infusion data reporting events.

One or more embodiments described herein may enhance the standard client-server communication model and allow a server to send a command request to a client.

One or more embodiments described herein may ensure the safety of the pump not to be controlled remotely except for specific commands that are not safety related.

One or more embodiments described herein may allow a remote server computer to send a command request to an infusion pump client, which is not supported in the Hypertext Transfer Protocol (HTTP) Request for Comments (RFC) client-server model.

One or more embodiments may provide improved functioning of the infusion pump and the server computer in communication with the infusion pump. In such embodiments, a computer on board the infusion pump is made more secure by blocking commands received over a network which are not sent in response to a request for command transmitted by the infusion pump. This can help prevent spoofing or other cyberattacks from unauthorized devices. The security of the computer on board the infusion pump can be improved over systems without this feature. On the server side, processing resources may be conserved until such time as an infusion pump makes a request for command to the server.

Figure 1:
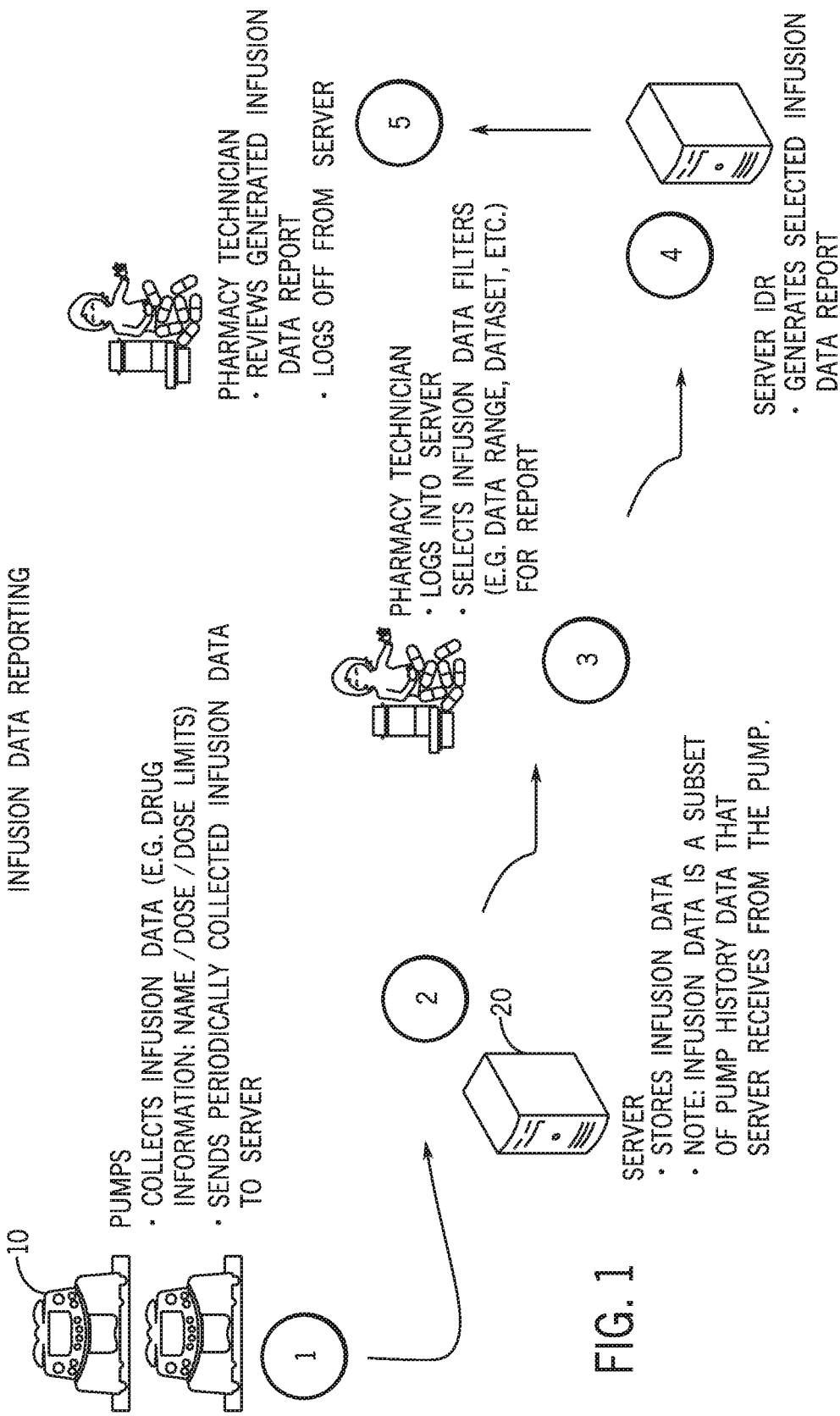
FIG. 1 is a flow diagram of a system for collecting infusion data from a plurality of infusion pumps at a server computer, according to an illustrative embodiment.

Referring now to FIG. 1, a flow diagram of a system for collecting infusion data from a plurality of infusion pumps at a server computer will be described. Infusion pump 10 may be any of a variety of infusion pumps, such as a large volume infusion pump, a patient-controlled analgesia (PCA) pump, elastomeric pump, syringe pump, enteral or parenteral feeding pump, insulin pump, etc. At Step 1 in FIG. 1, infusion pump 10 is configured to collect infusion pump data, such as infusion pump programming data (e.g., user key presses on a user interface thereof), events (e.g., a user entering a value, a user confirming a value, an alert, a notification, etc.), pump history data (e.g., any data related to pump functions) or other infusion pump data. Programming data can include drug name, dose, dose changes, start time, stop time, alarm information, etc. Alarm information may include a type of alarm, a start time for the alarm, a care area in which the pump was used during the alarm, a drug name of a drug being administered during the alarm, time to alarm resolution, etc.

At Step 2 in FIG. 1, infusion pump 10 may be configured for wired and/or wireless communication with a server computer 20. Each of pump 10 and server computer 20 may comprise a network interface circuit configured for network communications, such as a Wi-Fi circuit, Bluetooth circuit, Ethernet card, or other network interface circuit. Pump 10 is configured to transmit and server 20 is configured to receive infusion pump data over the respective network interface circuits. Server 20 is configured to store the infusion data from a plurality of infusion pumps, which may be in different care areas, for analysis, whether automated or by a clinician. Infusion data transmissions may be initiated by infusion pump 10 and may occur periodically, intermittently, occasionally, every few minutes, several times per day, or at other regular or irregular frequencies. Infusion data stored at server 20 may be a subset of pump history data that server 20 receives from pump 10.

At Step 3 in FIG. 1, a nurse, pharmacist, biomedical engineering staff, or other user may log into server 20 using a terminal (not shown), which may be a user interface for server 20 or may alternatively be a separate computing device or PC networked with server 20. The user opens an application configured to review infusion pump data or logs into a web page configured to communicate over an HTTP protocol with server 20. Server 20 may be configured to generate one or more reports based on analysis of the infusion pump programming data. Reports may be generated in a prescheduled manner or on-demand based on user inputs to the system. Reports may also be sent automatically, without requiring user input, on a scheduled basis, or in response to certain rules being met (e.g., alarm triggered, a certain number of alarms triggered, a certain number of override or reprogram events, etc.). The user may select one or more infusion data filters, such as hospital, data set, profile, drug, device type, infusion mode, time and/or date range, etc.

At Step 4 in FIG. 1, the server computer is configured to generate the selected infusion data report or reports.

At Step 5 in FIG. 1, a user analyzes the report data and may make changes to a data set or library used to program infusion pumps 10. For example, a data set may comprise hard limits and/or soft limits for-different pump programming parameters, such as infusion rate, dose, infusion time or duration, etc. The limits of the data set may be different for different drugs, and may include a "drug X" data set for a drug not known by the data library. Once changes are made to the data set or library, server 20 may be used to remotely download, update, or otherwise program infusion pumps 10 (e.g., by care area, universally, etc.) with the new data set changed by the pharmacist or other user at Step 4.

Figure 2:
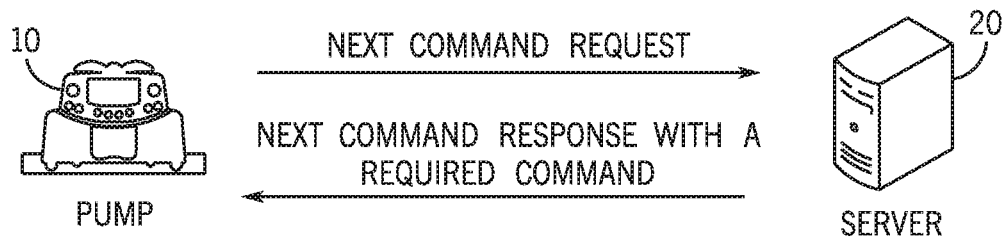
FIG. 2 is a block diagram of a system and method for providing secure network access to an infusion pump, according to an illustrative embodiment.

Referring now to FIG. 2, systems and methods for providing secure network access to an infusion pump will be described. As mentioned, each of pump 10 and server 20 comprises a network interface circuit configured for communication over a network, such as a hospital network. Routers or other networking components may be provided in the communication chain between pump 10 and server 20. In one embodiment, the interface between server 20 and pump 10 follows a strict client-server model of communication, in which pump 10 is always in the role of a client and the server is always in the role of a server computer. In alternative embodiments, the devices may change client and server roles, for example at different times or in different modes.

In an exemplary client-server model, the server component provides a function or service to one or many clients which initiate requests for services. Clients and servers may exchange messages in a request-response messaging pattern: client sends a request and the server returns a response. A HTTP protocol may be used in the application layer for the communication between the server and client pumps. Once a transmission control protocol (TCP) connection is created, two steps in communication comprise Request and Response. Pursuant to HTTP RFC, during a Request, the HTTP client sends a request message that specifies the resource that the client wishes to retrieve from the server or reports information to the server. During the Response, the HTTP server reads and interprets the request from the client. The server takes action relevant to the request and sends an HTTP Response message back to the client. The response message contains the content of the resource that the client requested, if appropriate.

In one embodiment, pump 10 is configured to transmit infusion data to server 20. After transmitting the infusion data, pump 10 is configured to send a request for any commands from server 20 to pump 10. This request for commands may be called a next command request, since it may request whether server 20 has any command to make after the infusion data report. In alternative embodiments, the request for command may be made prior to transmitting the infusion data, but after establishing a communication session.

According to one advantageous embodiment, because pump 10 initiates all communication requests with server 10, the risk of a cyberattack, such as a brute force attack, is minimized. At the same time, the protocol allows server 20 to make commands of pump 10 using the next command. Server may be configured to not make requests or commands on its own initiative, in keeping with a strict client/server model of communication. In one embodiment, pump 10 may be configured to block commands from any server computer which are not sent in response to the request for command transmitted by the infusion pump.

In some embodiments, the "Next" Command mechanism allows the server to send a command request to the pump client, which may not be supported in the HTTP RFC client-server model. In this example, the client pump uses the next command HTTP request to request additional commands from the server to execute. The server sends the next command HTTP response with the command that requires the client to execute.

In some embodiments, the server can create a next command HTTP response message when it needs the pump client to perform an action. For example, the server may be configured to detect that infusion data reporting events are missing and the server needs the pump to resend the pump history data containing the infusion data reporting events. The next command response message may not be sent to the pump client until the client sends a next command request to the server.

One mechanism for preventing cyberattacks on pump 10 is to close one, more or all of the communication ports provided by the network interface circuit of pump 10. A port may be an end-point of a communication, in software form, hardware form, or both. For example, in transmission control protocol/internet protocol (TCP/IP), a port is opened before communication may occur. By closing a communication port, a device does not receive communications on that port and therefore cannot be attacked. Another mechanism that may be used is a firewall, in which a software construct monitors communications and determines whether the communications should be received by the device. Yet another mechanism that may be used is a proxy, which is a program that evaluates incoming traffic to determine if it is safe for a network. Any of these mechanisms or other mechanisms may be used to block attempts to communicate with client pump 10.

Figure 3:
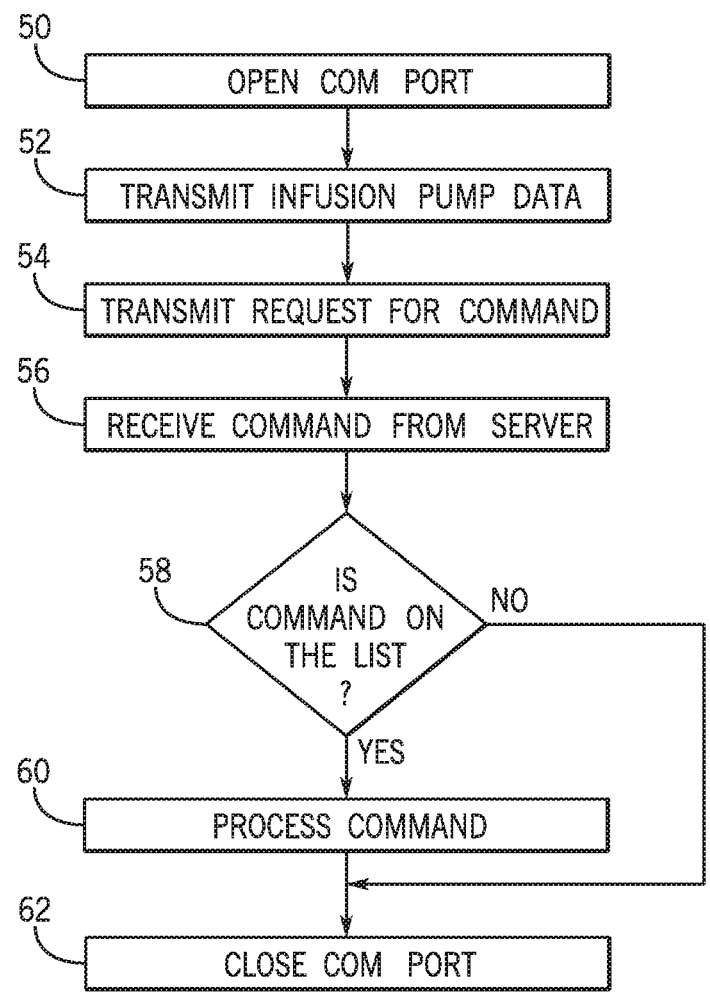
FIG. 3 is a flowchart of a client-side method of providing secure network access to an infusion pump, according to an illustrative embodiment.

Referring now to FIG. 3, a flowchart of a method of improving network access security will be described from a client-side perspective. At a block 50, a processing circuit of an infusion pump is configured to control a network interface circuit to open a communication port on the network interface circuit. The port may be defined in software and/or hardware, and the network interface circuit may be configured to provide or support a plurality of ports, which may be independently or collectively opened and closed. At a block 52, the processing circuit may be configured to transmit infusion pump data to a server computer over the network using the communication port which was opened. The infusion pump transmission may comprise any type of message or data, such as current time according to the infusion pump, current software version operating on the infusion pump, events that occurred on infusion pump since the last transmission, or other types of data.

At block 54, the processing circuit may be configured to transmit to the server computer a request for a command from the server computer. This may be the next command message referred to herein. This may be transmitted after the infusion pump data is transmitted, in between infusion pump data transmissions, or before the infusion pump data is transmitted. In one embodiment, the communication port remains open after transmission of the infusion pump data to allow transmission of the request for a command. In one embodiment, the communication session may remain open or active after transmission of the infusion pump data to allow transmission of the request for a command. In one embodiment, the processing circuit may be configured to keep one or more or all remaining communication ports closed while the communication takes place on the communication port which was opened.

At block 56, a command may be received from the server computer. The command may be a request to send infusion pump data. The command may be a request to perform a function with the infusion pump.

According to one embodiment, the commands that may be recognized by or implemented by infusion pump 10 may be limited to those on a predetermined list of commands, which is a subset of functions the infusion pump is configured to perform. For example, the predetermined list of commands may be commands that do not have an impact on safety of the infusion pump. For example, the list of commands may include a command to report the pump's current network connection status but exclude a command to start an infusion or change an infusion parameter.

At a block 58, the processing circuit is configured to determine whether the command received from server 20 is on a predetermined list of commands. The predetermined list of commands may include one, some or all of the following, or other commands:

TABLE 1

| Command | Description |
| --- | --- |
| Connection Status | Report pump's current network connection status to the server |
| Current Dataset Version | Report pump's current version of the dataset to the server |
| Current Time | Receive current time from the server |
| Dataset Programming Error | Inform the server of error in programming of new dataset |
| New Dataset File | Receive new dataset file |
| Pump Events | Send Infusion Data Report events to the server |
| Pump Mode | Send the current operating mode of the pump to the server |
| Response Error | Report any error occurred in the processing of server's response to the server |
| WiFi Events | Report pump's Wi-Fi module events to the server |
| WiFi Mode | Send current mode of WiFi module to the server |
| Empty | No command is required to execute |

Regarding connection status, the connections status may, for example, be connected, searching, disconnected, or other statuses. The dataset version may refer to a version number or other code indicating a version of a library of pump programming parameters that is currently stored on the infusion pump. Current time may refer to time of day. The Dataset Programming Error may refer to an indication that an error occurred when the infusion pump was being programmed with a dataset or library, whether from a local computer (e.g., via wired or wireless connection) or via a remote provisioning or programming server. New Dataset File may refer to a command that the infusion pump prepare for receipt of a new dataset or library, for example to replace a previously loaded infusion dataset. Pump Events may include such items as an indication that a user programmed a parameter outside of a hard or soft programming limit defined by the dataset or library, an indication that a user started an infusion with the pump, an indication that an error occurred during the infusion or programming, etc. Each pump event may comprise a plurality of fields of data, such as time/date of the event, an event code, a description of the event, and additional pump data associated with the event (e.g., the value that was programmed when the hard or soft limit was exceeded).

Pump operating modes may include an indication that the pump is currently in a programming mode, an idle mode, an infusing mode, a maintenance mode, or other modes. Exemplary Wi-Fi Events may include one or more Wi-Fi network connection errors, Wi-Fi network connection status, etc. Wi-Fi modes may include, for example, ON, ON BATTERY, etc. An Empty message may indicate that server 20 has no command for infusion pump.

At a block 60, the processing circuit is configured to process the command. Processing the command may include any of a variety of operations, such as retrieving additional infusion pump data from memory, generating a report, compiling data, storing data, transmitting data to the server computer or to another computer, etc.

At a block 62, the processing circuit may be configured to close the communication port which was opened in block 50. The port may also be closed after block 58 in the event the received command is not on the predetermined list.

The blocks described above and in FIG. 4 may be rearranged in various alternative embodiments and need not be implemented in the prescribed order in all embodiments.

Figure 4:
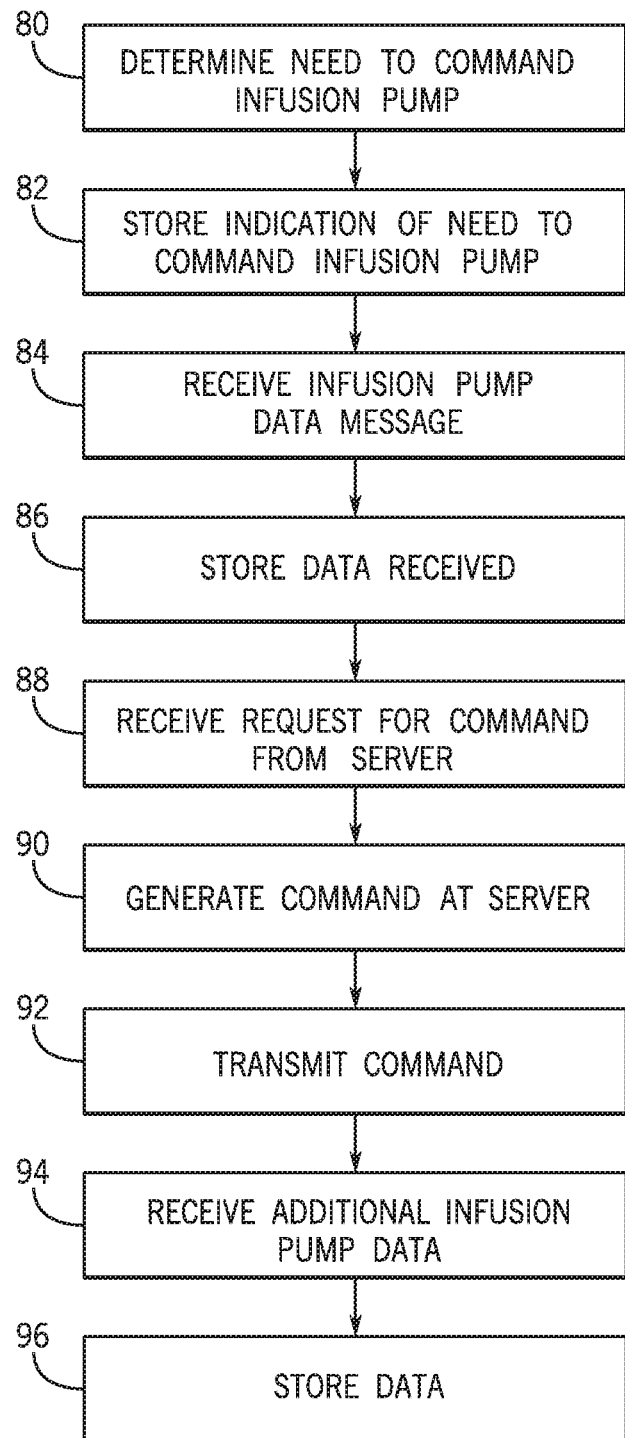
FIG. 4 is a flowchart of a client-side method of providing secure network access to an infusion pump, according to an illustrative embodiment.

Referring now to FIG. 4, a server computer with improved network access security to an infusion pump will be described with reference to a flowchart of blocks operational on the server computer. At a block 80, the processing circuit of the server may be configured to determine a need to command an infusion pump and, at block 82, store an indication of the need to command the infusion pump in a memory. The need may arise from any of a number of circumstances. For example, server 20 may be processing infusion data (e.g., events or other data) and determine that additional infusion data events are missing or needed. As another example, a user may command server 20 to update data files on one or more infusion pumps, leading to a need to command an infusion pump to receive a new data set. As another example, server 20 may be configured to periodically command infusion pumps to receive a current time of day from server 20 to ensure the time of day of the pump is accurate. The indication of a need may be a software flag, data element, word, command or data structure that indicates server 20 is to send a command to pump 10, typically at the next communication session established at the request of pump 10. The server computer may be configured to hold or store the indication of the need to command the infusion pump in a memory until a request for a command is received from the client computer.

After storing the indication of the need to command the infusion pump in memory, the processing circuit may be configured to receive an infusion pump data message from an infusion pump at a block 84. The server may be configured to maintain an open port for communication requests from infusion pumps 10. The server itself may be configured to operate a firewall, close certain ports, use a proxy server, or provide one or more other security mechanisms to prevent spoofing or other attacks on the server. After receiving a communication request (e.g., via HTTP over TCP/IP) and establishing a communication session (e.g., a secure communication session, such as SSL), server 10 may be configured to receive the message from an infusion pump which, in this example, comprises infusion pump data (e.g., event data reporting, programming data, alerts, etc.). At a block 86, the server 10 is configured to store the infusion pump data from the message in a memory, such as a database, such as a relational database.

At a block 88, server 20 may be configured to receive a request for a command from the infusion pump. The request for a command may be a next command as described herein. The request may be generated by the infusion pump and may provide an instruction or command to server 20 that pump is ready to receive a command during the existing communication session. In some embodiments, the infusion pump may only maintain an open channel or port for communication for a predetermined time period before expiring and closing the port.

At a block 90, server 20 may be configured to generate an infusion pump command based on the need to command the infusion pump. For example, if the indication of a need for a command indicates that certain infusion data reporting events are needed, the command may include an indication of which infusion data reporting events are needed, or that all infusion data reporting events are to be retransmitted from pump 10 to server 20. The command may take any of a variety of forms, for example including a header, payload, checksum, and/or other message characteristics.

At a block 92, the processing circuit is configured to transmit the infusion pump command to the infusion pump over the network during the communication session with the infusion pump port which was opened for communication. The server may resend the command periodically as needed to achieve a response, and may timeout if a response is not received within a predetermined period of time. At a block 94, the processing circuit is configured to receive additional infusion pump data in response to the infusion pump command and, at block 96, to store the additional infusion pump data in memory. Not all next commands will necessitate a response, indicating these steps are optional in alternative embodiments. Further, not all responses will comprise infusion pump data that needs to be stored or recorded. In this example, however, additional infusion data is received and stored and may be used to generate automatic or user-requested reports for further analysis. In one embodiment, the processing circuit is further configured to receive a user request for a report (e.g., via a user interface, perhaps using filters or other data specifications) and to generate report data for display comprising the infusion pump data and the additional infusion pump data. For example, the report may show some infusion data events received, for example, at block 84 and additional infusion data events received, for example, at block 94.

According to one exemplary embodiment, server computer 20 may be configured to not send any command to the infusion pump except in response to receiving the request for command from the infusion pump.

Figure 5:
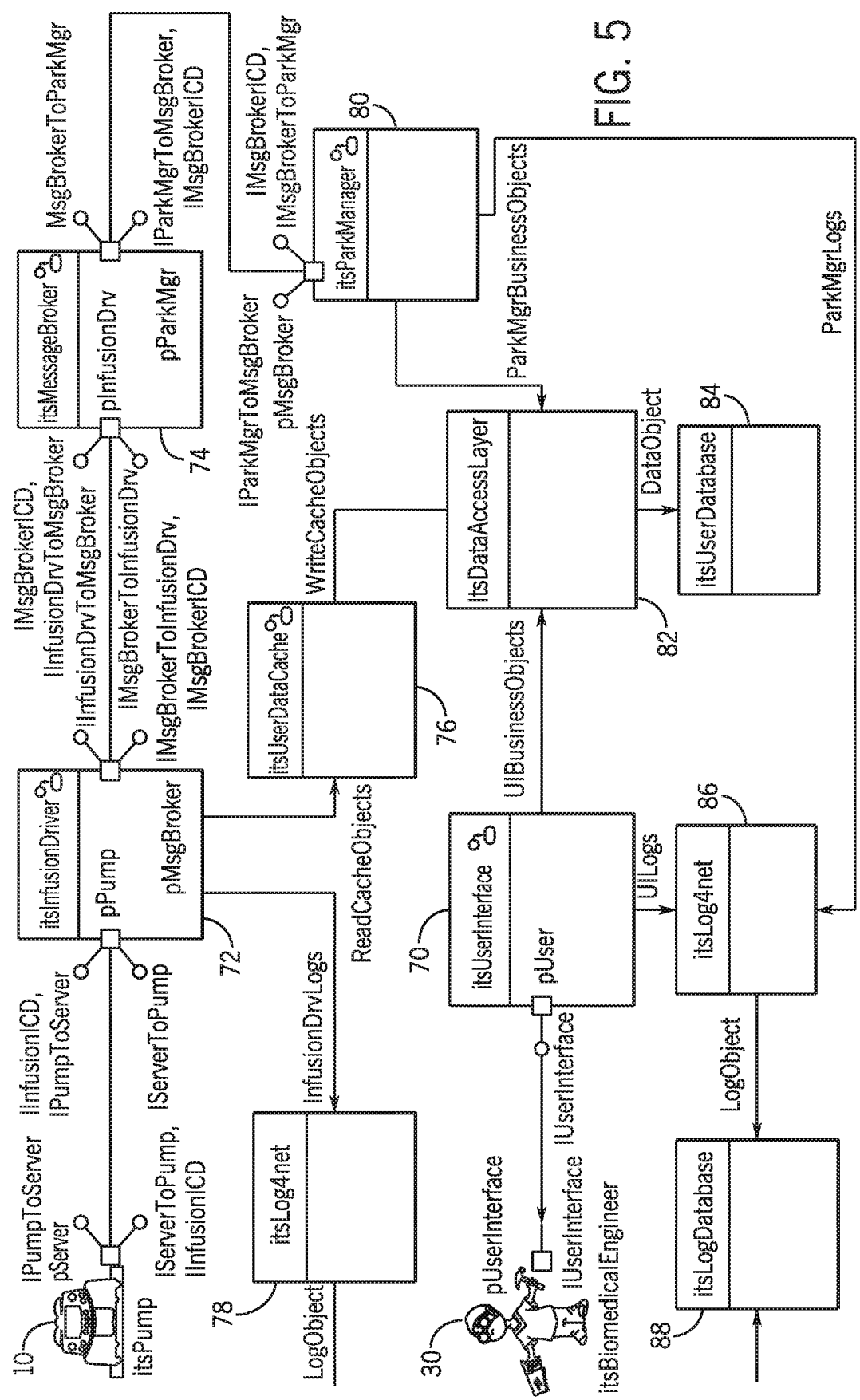
FIG. 5 is a flow diagram illustrating instances of server components configured to provide functionalities described herein, according to an illustrative embodiment.
Figures 6A, 6B:
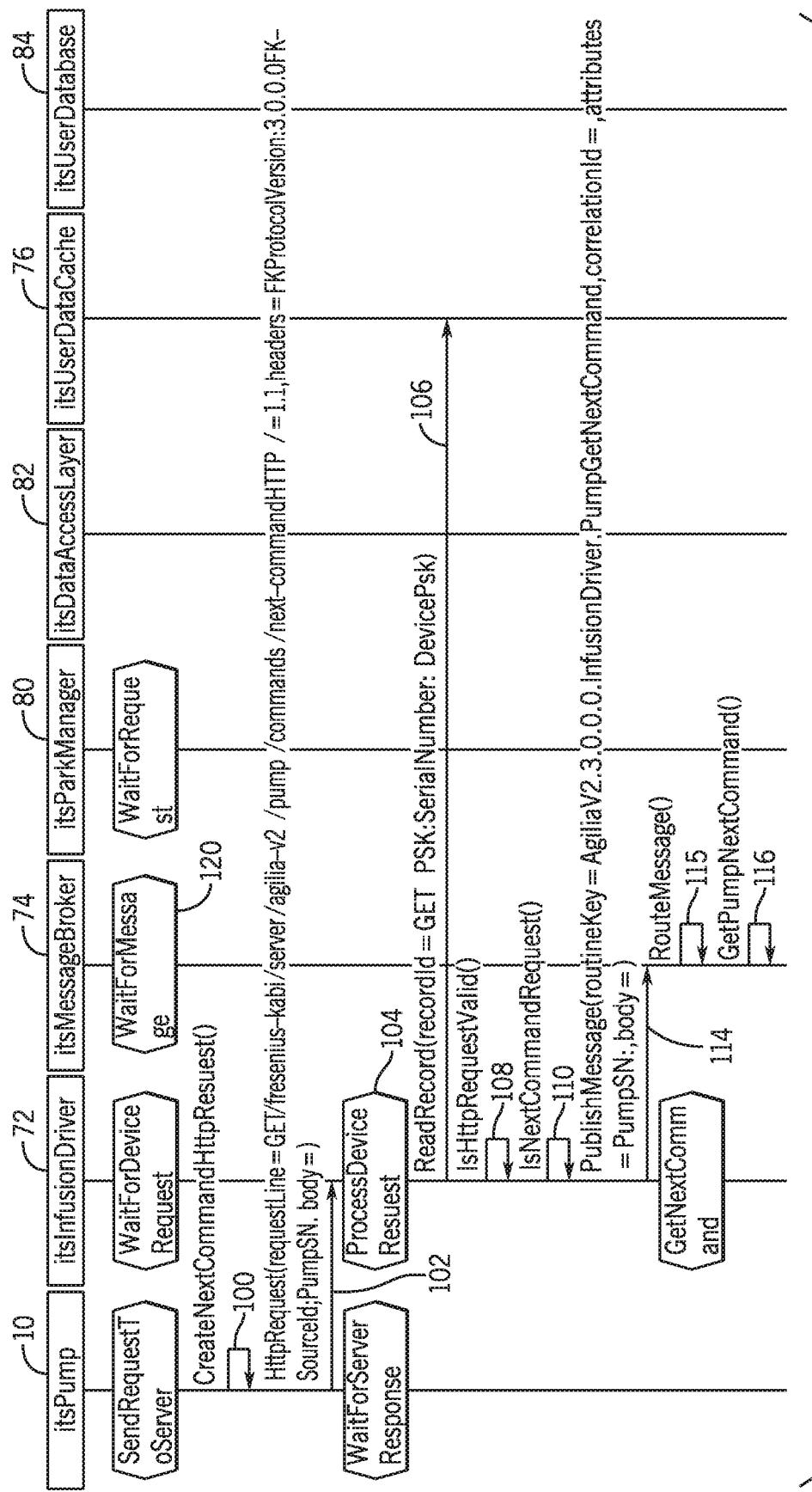
FIGS. 6A-6D show a diagram of a communication process, according to one illustrative embodiment.
Figure 6B:
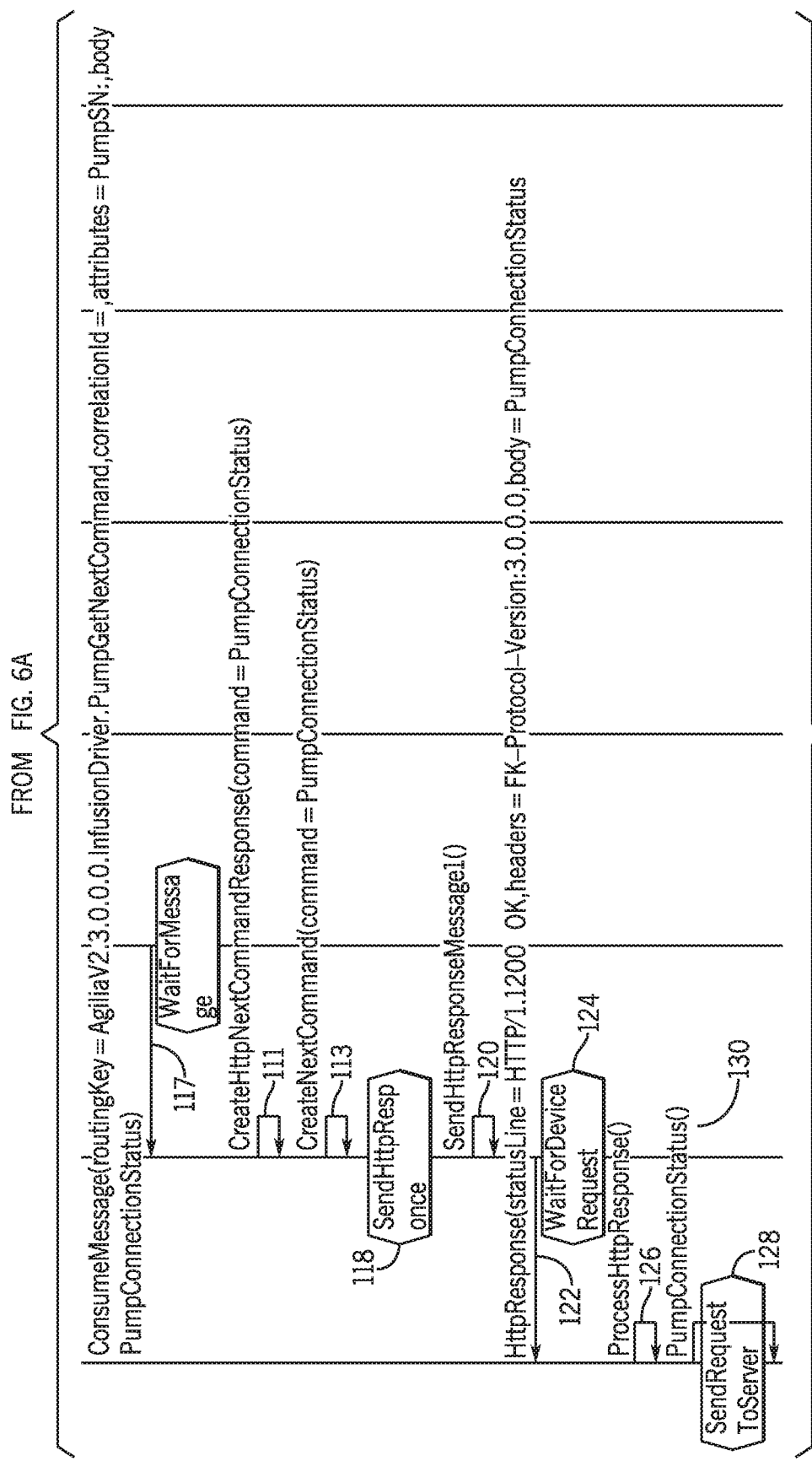
Figure 6C:
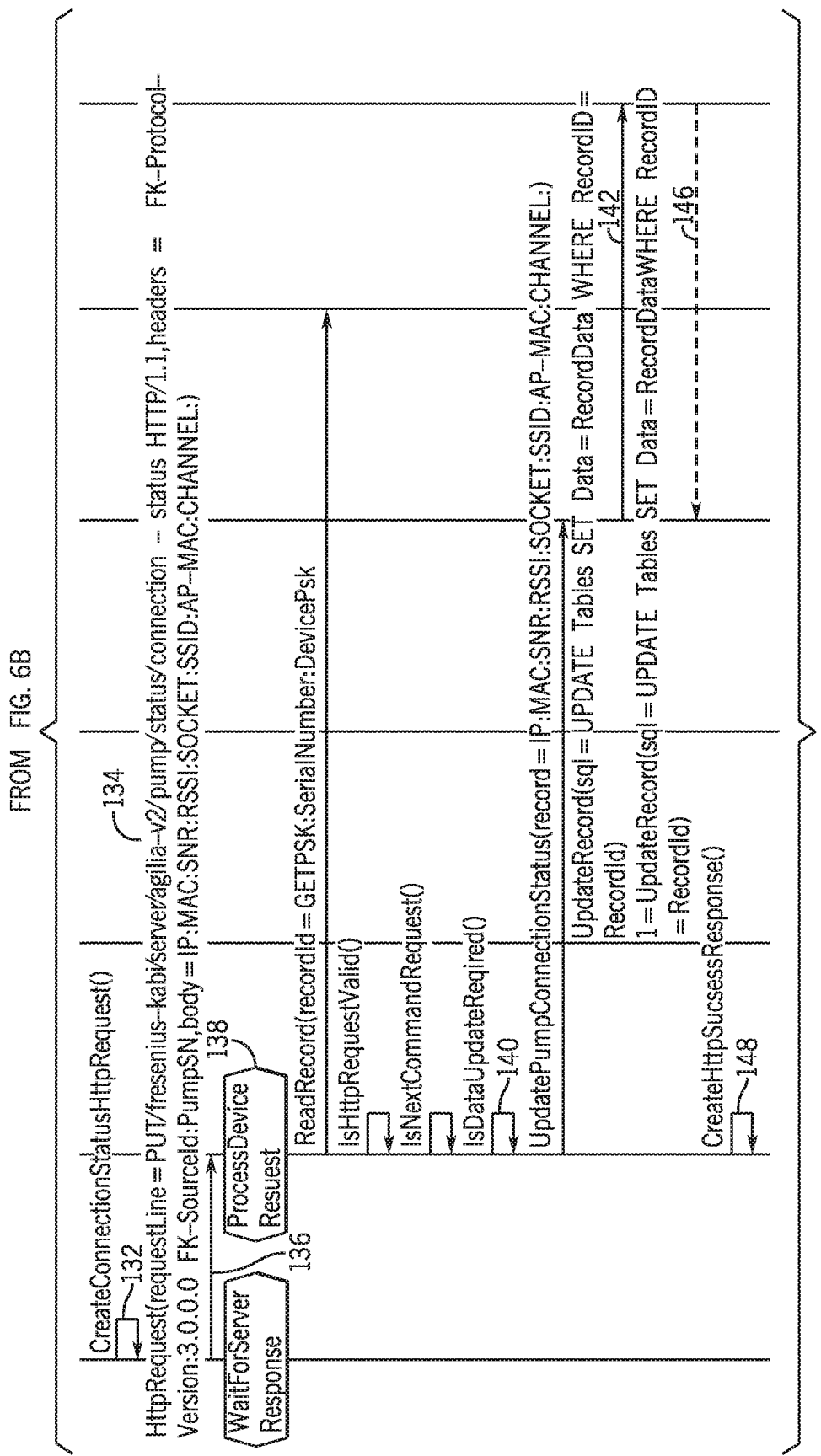
Figure 6D:
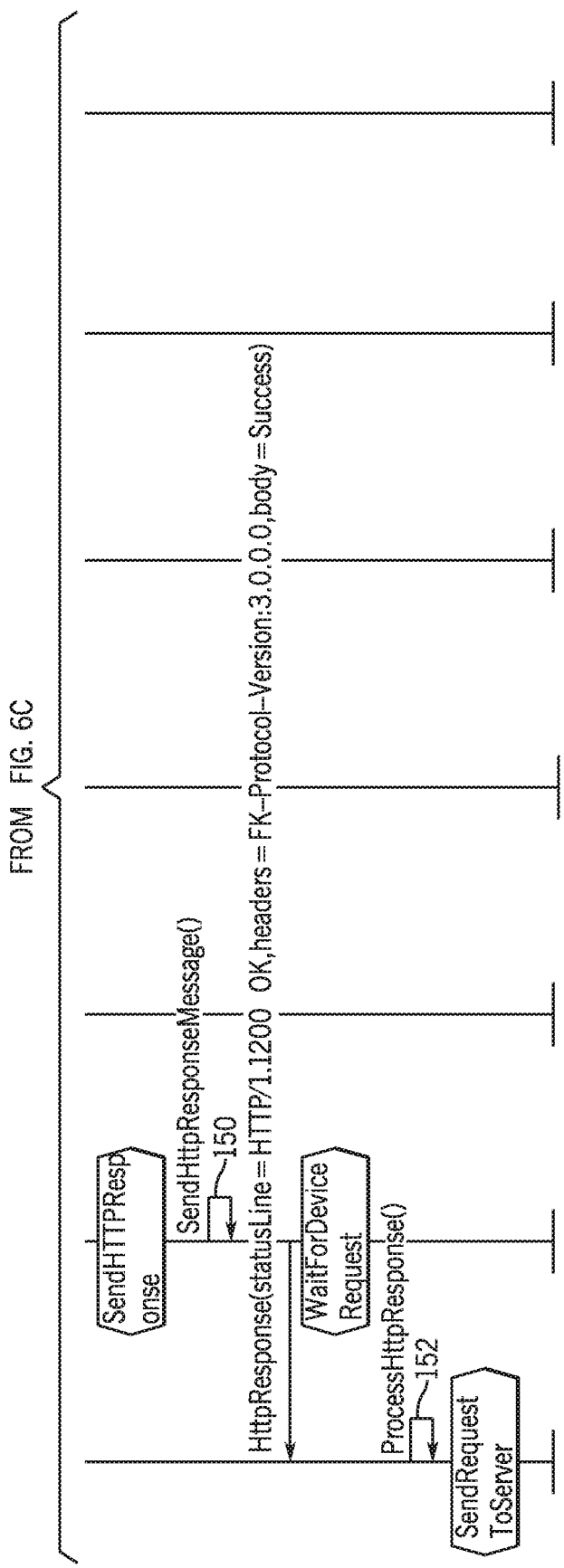

Referring now to FIG. 5, a flow diagram illustrating instances of server components configured to provide functionalities described herein will be described, according to an illustrative embodiment. The components are configured to receiving monitoring statuses from deployed pump(s) and display current status via a user interface to a biomedical engineer 30. Functions related to status display are handled by the server components via the provided user interface component 70 to a display viewable by the biomedical engineer or other user. Functions related to receiving status from infusion devices are provided via the InfusionDriver interface component 72. Shared commonly across the system are logging and data access functions, such as a message broker 74, a user data cache 76, an infusion driver log 78, a manager 80, a data access layer 82, a user database 84, a user interface log 86 and a log database 88. The server components shown here will be used to describe an exemplary embodiment with reference to FIGS. 6A-6D.

FIGS. 6A-6D illustrate an exemplary algorithm for use of the next command to obtain an indication of pump connection status success. At line 100, pump 10 is configured to operate a function that creates a next command HTTP request. At line 102, pump 10 transmits the created HTTP request to infusion driver 72. In this example, the request is to get a resource from the server from a next-command resource location. If the server has placed any requests into that location, this request will obtain the first of those requests. The request includes a request line identifying the resource location, a protocol version and one or more headers which may indicate a protocol version and source ID which identifies the pump 10, which may comprise a serial number. At block 104, infusion driver 72 is configured to process the device request. At a line 106, a record is read from user data cache 76 to obtain the device serial number for the device that made the request. At a line 108, infusion driver 72 is configured to determine whether the HTTP request is a valid request (e.g., has the proper format, is authentic, etc.). At a line 110, infusion driver 72 is configured to determine whether a next command request is present in the HTTP request.

At a line 114, infusion driver 72 is configured to publish the message to message broker 74 which has been waiting for a message (per block 120). This function pushes the message onto a queue of message broker 74 which simplifies operation of infusion driver 72. At a line 115, broker 74 routes the message and, at line 116, broker 74 gets the command the server has stored for the pump. At line 117, broker 74 sends the retrieved command to infusion driver 72. Drive 72 then creates (lines 111, 113) the next command response containing the command, which in this case is a request for pump connection status data.

Infusion driver 72 is configured to generate an HTTP Response message for sending back to pump 10 (block 118 and line 120). Line 122 represents the response being sent to pump 10 which contains the pump connection status request in the body of the response message. Infusion driver 72 returns to a "wait for request" mode at block 124.

At line 126, pump 10 processing the response message from driver 72. Pump 10 retrieves pump connection status data and starts generating a request message (function 130 and block 128). At function 132, pump 10 generates a connection status HTTP Request, which is shown at request 134. The request comprises a request line identifying a resource location as pump/status/connection-status, headers comprising protocol version and source ID, and a body comprising the connection status data, which may comprise one or more of an IP address, a MAC address, a signal to noise ratio, a received signal strength indicator, a socket ID, a service set ID, a channel, etc. This request is sent (line 136) to driver 72 which processes the request (block 138) in a manner similar to step 106, 108 and 110 above.

A function 140 determines whether the message comprises data such that an update to a database is required. If so, driver 72 generates an update pump connection status message and transmits the message (comprising the connection status data) to data access layer 82, which records the data in user database 84 (lien 142). Database 84 confirms the update to data access layer 76 via line 146.

Driver 72 generates a success response at line 148 and sends the response (line 150) to pump 10. Pump processes the request at line 152. In a typical HTTP client-server communication, a response such as shown at line 148 would terminate the communication. In one example, pump 10 may be configured to, after processing the request at line 152, generate another next command request. Next command requests may be repeatedly generated by pump 10 after receiving next command responses until a next command response indicates no further next commands are needed, or the next command queue is empty. Pump 10 may then return to other pump functions.

In this example, the command issued by the server using the next command function was a request for pump connection status. In alternative embodiments, other commands may be issued, such as a request for current version of a dataset, and other commands such as those listed in Table 1 herein.

Figure 8:
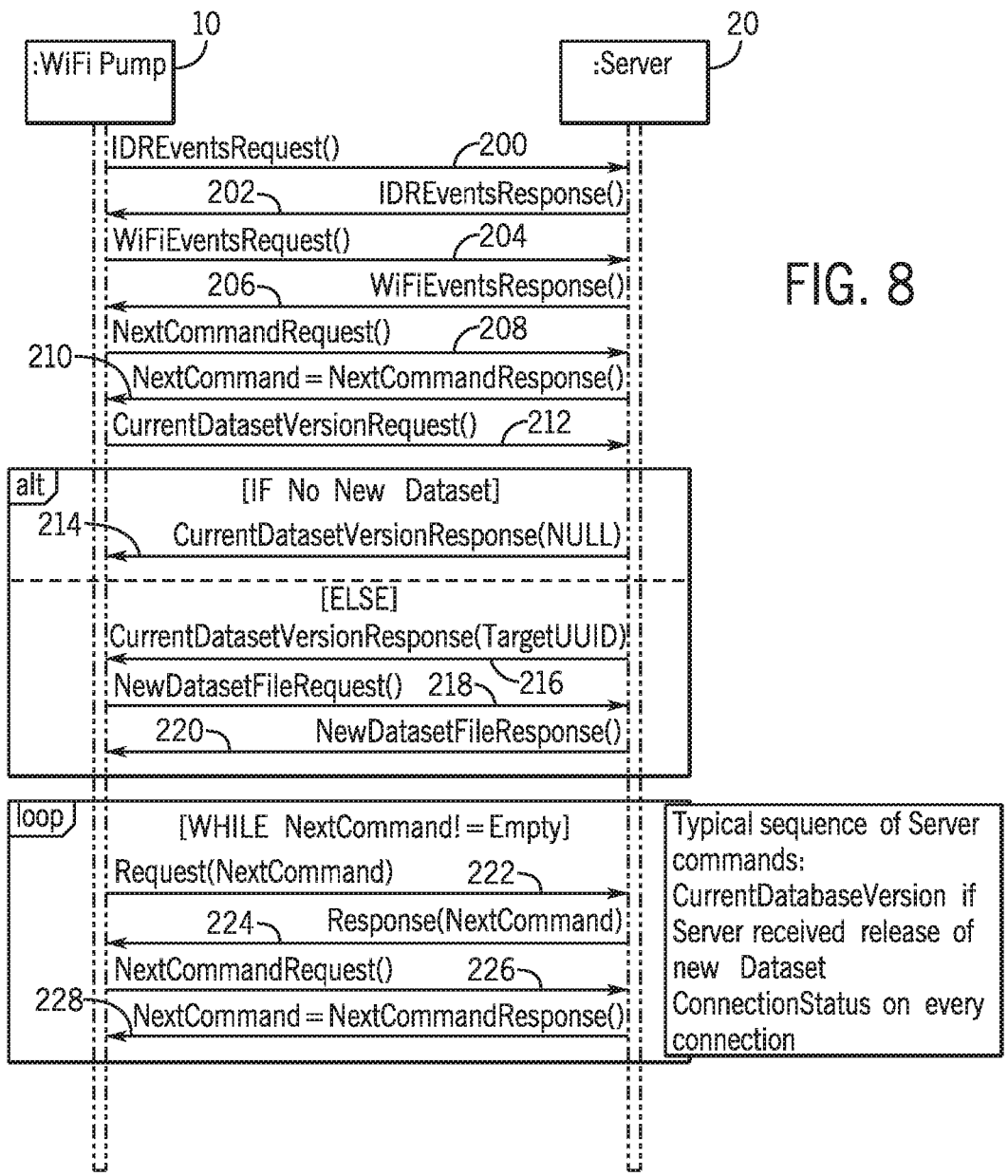
FIG. 8 is a diagram of a communication process, according to one illustrative embodiment.

FIG. 8 illustrates a sequence of requests and responses between pump 10 and server 20 according to an exemplary embodiment. In this example, pump 10 is configured to continuously send requests for commands (e.g., next commands) to server 20 until server 20 returns a null, zero, or other indication that there is no new command server 20 has in a queue for pump 10. In one embodiment, each of a plurality of consecutive requests sent by pump 10 to server 20 (or every request) may be followed by a request for command (e.g., next command) sent to server 20.

At line 200, pump 10 is sending an infusion data reporting (IDR) events request to server 20. The IDR events may comprise such things as an indication that an infusion has been started (e.g., along with infusion data, such as flowrate, estimated time to completion of infusion, time infused so far, etc.), an indication that a hard or soft limit has been exceeded by a user using a user interface on pump 10, alerts, or other events. Server 20 may log these events for future reporting and generate an IDREventsResponse message to notify pump 10 the data has been logged. Pump 10 may have another request queued which is sent after its previous request has been responded to, which is shown here as a WIFIEventsRequest message. This message reports Wi-Fi events that occurred on pump 10 to server 20, again for logging, storing, reporting, analysis, etc. Server 20 generates a response message to confirm the logging 206.

When pump 10 has exhausted its queue of requests or otherwise has no further requests of pump 20, pump 10 may be configured to send a NextCommandRequest, such as shown at line 208. Server 20 processes the NextCommandRequest by checking a queue stored in memory for any command or commands that server 20 has stored for pump 10. If one exists, the response message containing the command is sent (line 210). In this example, the command is a request for a current dataset version. Pump 10 responds (line 212) to the response by generating an HTTP request message with the current dataset version indication in the body of the message. Server 20 is configured to determine whether a new dataset version is available for pump 10 and, if not, server 20 sends a CurrentDatasetVersionResponse (NULL) message at line 214. If a new dataset is available, at line 218, pump 10 sends a request message for the new dataset using a resource locator received in response message 216, shown in this example as a Universally Unique Identifier (UUID). Server 20 responds with a download of the new dataset file at line 220.

After processing the response from message 220, pump 10 may be configured to generate another request for a command (e.g., a next command) from server and send it at line 222. So long as the response to the next command request is not empty, null, or otherwise indicates there are no further commands server 20 has for pump 10, additional requests for next command will be sent and processed (the processing shown at lines 226 and 228). In some embodiments, each or every of a plurality of requests sent by pump 10 to server 20 will, after the response is processed, be followed by a request for commands (e.g., a next command). In some embodiments, pump 10 will continue to send requests for commands after processing responses until no further commands are stored at server 10 for pump 10.

Figure 7:
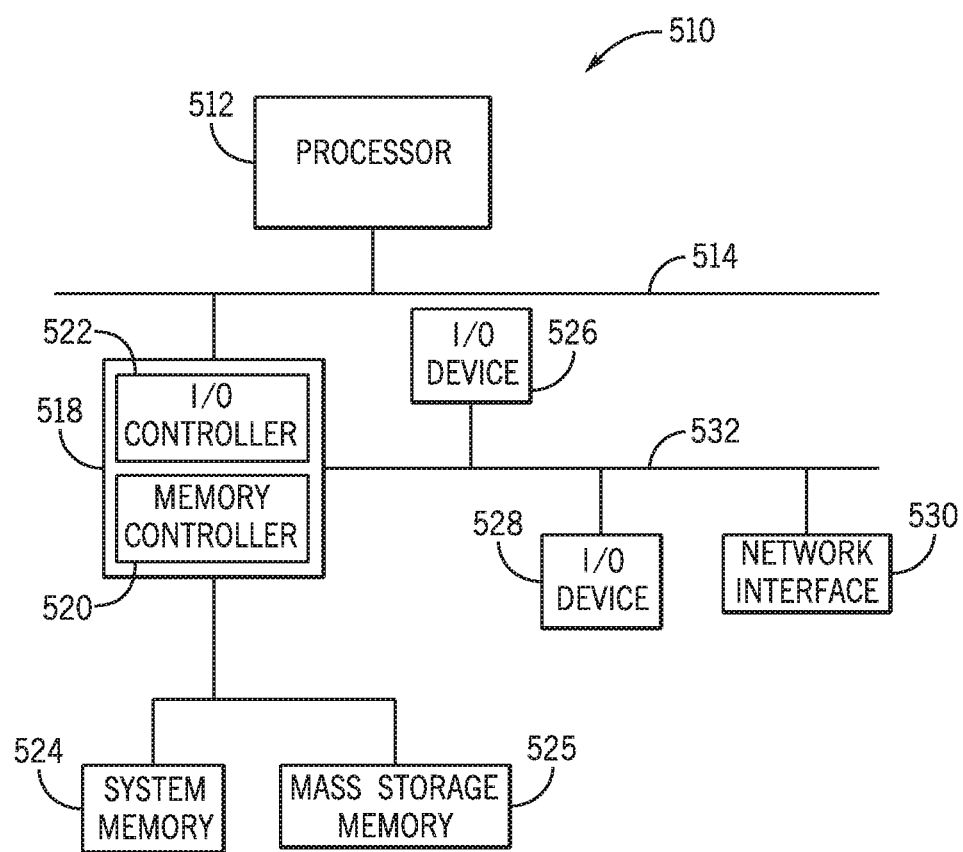
FIG. 7 is a block diagram of a computing device usable as client or server computer, according to an illustrative embodiment.

FIG. 7 is a block diagram of a server computer for processing infusion pump data for presentation on a display, according to an illustrative embodiment. In alternate embodiments, the systems and methods described herein may be implemented on a single server computer, a plurality of server computers, a server farm, a cloud server environment, or using other computer resources. Server 20 and infusion pump 10 may comprise analog and/or digital circuit components forming processing circuits configured to perform the steps described herein. The processing circuits may comprise discrete circuit elements and/or programmed integrated circuits, such as one or more microprocessors, microcontrollers, analog-to-digital converters, application-specific integrated circuits (ASICs), programmable logic, printed circuit boards, and/or other circuit components. Server 20 and infusion pump 10 each may comprise a network interface circuit configured to provide communications over one or more networks with each other and/or with other devices. The network interface circuit may comprise digital and/or analog circuit components configured to perform network communications functions. The networks may comprise one or more of a wide variety of networks, such as wired or wireless networks, wide area-local-area or personal-area networks, proprietary or standards-based networks, etc. The networks may comprise networks such as an Ethernet network, networks operated according to Bluetooth protocols, IEEE 802.11x protocols, cellular (TDMA, CDMA, GSM) networks, or other network protocols. The network interface circuits may be configured for communication of one or more of these networks and may be implemented in one or more different sub-circuits, such as network communication cards, internal or external communication modules, etc.

According to one embodiment, storage of the infusion data records may be implemented on a database coupled to or part of server 20. The database may be a DBMS hosted on a server host platform, such as Microsoft Windows XP, Microsoft Windows Server 2008, etc.

Referring again to FIG. 7, a block diagram of an example processor system 510 is shown that can be used to implement systems, articles of manufacture, and methods described herein. As shown in FIG. 7, the processor system 510 includes a processor 512 that is coupled to an interconnection bus 514. The processor 512 can be any suitable processor, processing unit, or microprocessor, for example. Although not shown in FIG. 7, the system 510 can be a multi-processor system and, thus, can include one or more additional processors that are identical or similar to the processor 512 and that are communicatively coupled to the interconnection bus 514.

The processor 512 of FIG. 7 is coupled to a chipset 518, which includes a memory controller 520 and an input/output ("I/O") controller 522. A chipset may provide I/O and memory management functions as well as a plurality of general purpose and/or special purpose registers, timers, etc. that are accessible or used by one or more processors coupled to the chipset 518. The memory controller 520 performs functions that enable the processor circuit 512 (or processors if there are multiple processors) to access a system memory 524 and a mass storage memory 525.

The system memory 524 can include any desired type of volatile and/or non-volatile memory such as, for example, static random access memory (SRAM), dynamic random access memory (DRAM), flash memory, read-only memory (ROM), etc. The mass storage memory 525 can include any desired type of mass storage device including hard disk drives, optical drives, tape storage devices, etc.

The I/O controller 522 performs functions that enable the processor 512 to communicate with peripheral input/output ("I/O") devices 526 and 528 and a network interface 530 via an I/O bus 532. The I/O devices 526 and 528 can be any desired type of I/O device such as, for example, a keyboard, a video display or monitor, a mouse, etc. The network interface 530 can be, for example, an Ethernet device, an asynchronous transfer mode device, an 802.11 device, a DSL modem, a cable modem, a cellular modem, etc. that enables the processor system 510 to communicate with another processor system.

While the memory controller 520 and the I/O controller 522 are depicted in FIG. 7 as separate blocks within the chipset 518, the functions performed by these blocks can be integrated within a single semiconductor circuit or can be implemented using two or more separate integrated circuits.

Certain embodiments contemplate methods, systems and computer program products on any machine-readable media to implement functionality described above. Certain embodiments can be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a tangible machine accessible or readable medium and executable by, for example, a processor system (e.g., the example processor system 510 of FIG. 7). Tangible computer readable media include a memory, DVD, CD, etc. storing the software and/or firmware, but do not include a propagating signal.

As used herein, the term tangible computer readable medium includes any type of computer readable storage and excludes propagating signals. Additionally or alternatively, the example processes described herein may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information).

Certain embodiments described herein can omit one or more of the method steps and/or perform the steps in a different order than the order listed. For example, some steps cannot be performed in certain embodiments. As a further example, certain steps can be performed in a different temporal order, including simultaneously, than listed above.

While the exemplary embodiments have been described with reference to an infusion pump, the next command and other teachings herein may be applied to other medical devices, such as apheresis devices (e.g., plasmapheresis, apheresis, blood therapy, etc.) or other devices that are invasive or noninvasive, that interface with a human patient via a needle in the patient's skin, insulin pumps (e.g., internal or external to the body cavity), medical imaging devices (e.g., CT scanners, x-ray imagers, magnetic resonance imaging). The teachings may also be applied outside the medical field to any computing devices requiring an improved security solution, such as mobile phones, tablet computers or other computers configured to be operated while held in a human hand, laptops, personal computers, and other networked computers.

While the embodiments have been described with reference to certain details, it will be understood by those skilled in the art that various changes can be made and equivalents can be substituted without departing from the scope described herein. In addition, many modifications can be made to adapt a particular situation or material to the teachings without departing from its scope. Therefore, it is intended that the teachings herein not be limited to the particular embodiments disclosed, but rather include additional embodiments falling within the scope of the appended claims.

What is claimed is:

1. A method of improving network access security on an infusion pump, comprising:
    opening a communication port on a network interface circuit of an infusion pump to establish a communication session on a network;
    transmitting infusion pump data to a server computer over the network during the communication session;
    after the infusion pump data is transmitted to the server, transmitting to the server computer a request for a command from the server computer during the communication session;
    receiving a command from the server computer;
    determining whether the command is on a predetermined list of commands, the predetermined list of commands being a subset of functions the infusion pump is configured to perform;
    processing the command; and
    closing the communication port on the network interface circuit.

2. The method of claim 1, wherein the method further comprises, after processing the command, closing all communication ports provided by the network interface circuit.

3. The method of claim 1, wherein the command is processed by retrieving additional infusion pump data from memory and transmitting the additional infusion pump data to the server computer.

4. The method of claim 1, wherein the predetermined list of commands comprises a command to report a dataset version operable on the infusion pump, a command to receive a new dataset file, and a request for infusion events that occurred during an infusion process, wherein the list of commands excludes a command to start an infusion.

5. The method of claim 1, wherein the network interface circuit is configured to block commands from the server computer which are not sent in response to the request for command transmitted by the infusion pump.

6. The method of claim 1, wherein the infusion pump is configured to use a hypertext transfer protocol when communicating with the server computer.

7. The method of claim 1, wherein the method further comprises, after processing the command, transmitting another request for command to the server.

8. The method of claim 7, further comprising continuing transmitting requests for commands after processing commands until such time as an indication of no further commands is received from the server.

9. A method of improving network access security on a server computer, comprising:
    determining a need to command an infusion pump;

storing an indication of the need to command the infusion pump in a memory;

after storing the indication of the need to command the infusion pump in memory, establishing a communication session with the infusion pump to receive an infusion pump data message from an infusion pump;

storing infusion pump data from the message in the memory;

after storing the infusion pump data, receiving a request for a command from the infusion pump during the communication session;

generating an infusion pump command based on the indication of the need to command the infusion pump;

transmitting the infusion pump command to the infusion pump;

receiving additional infusion pump data in response to the infusion pump command; and storing the additional infusion pump data in memory.

10. The method of claim 9, further comprising receiving a user request for a report and generating report data for display comprising the infusion pump data and the additional infusion pump data.

11. The method of claim 9, further comprising holding the indication of the need to command the infusion pump in memory until the request for a command is received from the client computer.

12. The method of claim 9, wherein the infusion pump command is a request for a current version of an operating parameter library stored in the infusion pump.

13. The method of claim 9, wherein the infusion pump command is a request for events that occurred during infusion operations.

14. The method of claim 13, wherein determining the need to command the infusion pump occurs in a case where previously received infusion pump data indicate an event is missing from the previously received infusion pump data.

15. The method of claim 9, wherein the server computer does not send any command to the infusion pump except in response to receiving the request for command from the infusion pump.

16. The method of claim 9, wherein the infusion pump command is a request for a network connection status of the infusion pump.

17. A method of improving network access security on a medical device, comprising:

opening a communication port on the medical device to establish a communication session on a network;

transmitting medical device data to a computer over the network during the communication session;

after the medical device data is transmitted to the computer, transmitting to the computer a request for a command from the computer during the communication session;

receiving a command from the computer;

processing the command; and closing the communication port on the medical device.

18. The method of claim 17, wherein the method further comprises, after processing the command, closing all communication ports provided by the medical device.

19. The method of claim 17, further comprising determining whether the command is on a predetermined list of commands, the predetermined list of commands being a subset of functions the medical device is configured to perform, wherein the predetermined list of commands comprises a command to report a dataset version operable on the medical device, wherein the list of commands excludes a command to start a procedure on the medical device.

20. The method of claim 17, wherein the medical device is configured to block commands from the computer which are not sent in response to the request for command transmitted by the medical device.

* * * * *